United States Patent [19]

Moutafis et al.

[11] Patent Number: 5,333,620
[45] Date of Patent: Aug. 2, 1994

[54] HIGH PERFORMANCE PLASTIC COATED MEDICAL GUIDEWIRE

[75] Inventors: Timothy E. Moutafis, Gloucester, Mass.; Richard K. Elton; Thomas C. DuBois, both of Glens Falls, N.Y.; Bruce N. MacMore, South Glen Falls, N.Y.

[73] Assignee: C. R. Bard, Inc., Murray Hill, N.J.

[21] Appl. No.: 118,131

[22] Filed: Sep. 8, 1993

Related U.S. Application Data

[63] Continuation of Ser. No. 784,921, Oct. 30, 1991, abandoned.

[51] Int. Cl.$^5$ .................................................. A61B 5/00
[52] U.S. Cl. ................................................... 128/772
[58] Field of Search ...................... 128/657, 658, 772; 604/164, 170, 180, 280–282

[56] References Cited

U.S. PATENT DOCUMENTS

| | | | |
|---|---|---|---|
| 3,789,841 | 2/1974 | Antoshkiw | 128/2.05 R |
| 3,802,440 | 4/1974 | Salem et al. | 128/351 |
| 3,841,308 | 10/1974 | Tate | 128/2 M |
| 3,924,632 | 12/1975 | Cook | 128/348 |
| 3,941,119 | 3/1976 | Corrales | 128/2 M |
| 3,973,556 | 8/1976 | Fleischhacker et al. | 128/2 M |
| 4,020,829 | 5/1977 | Willson et al. | 128/2 M |
| 4,080,706 | 3/1978 | Heilman et al. | 29/173 |
| 4,085,757 | 4/1978 | Pevsner | 128/325 |
| 4,169,464 | 10/1979 | Obrez | 128/657 |
| 4,204,528 | 5/1980 | Termanini | 128/6 |
| 4,211,741 | 7/1980 | Ostoich | 264/173 |
| 4,257,421 | 3/1981 | Beal | 128/348 |
| 4,283,447 | 8/1981 | Flynn | 428/36 |
| 4,345,602 | 8/1982 | Yoshimura et al. | 128/349 R |
| 4,385,635 | 5/1983 | Ruiz | 128/658 |
| 4,419,095 | 12/1983 | Nebergall et al. | 604/96 |
| 4,425,919 | 1/1984 | Alston, Jr. et al. | 128/658 |
| 4,464,176 | 8/1984 | Wijayarathna | 604/164 |
| 4,504,268 | 3/1985 | Herlitze | 604/170 |
| 4,531,943 | 6/1985 | Van Tassel et al. | 604/280 |
| 4,534,363 | 8/1985 | Gold | 128/772 |
| 4,545,390 | 10/1985 | Leary | 128/772 |
| 4,563,181 | 1/1986 | Wijayarathna et al. | 604/280 |
| 4,682,607 | 7/1987 | Vaillancourt et al. | 128/772 |
| 4,721,117 | 1/1988 | Mar et al. | 128/772 |
| 4,757,827 | 7/1988 | Buchbinder et al. | 128/772 |
| 4,763,647 | 8/1988 | Gambale | 128/657 |
| 4,779,628 | 10/1988 | Machek | 128/772 |
| 4,813,434 | 3/1989 | Buchbinder et al. | 128/772 |
| 4,815,478 | 3/1989 | Buchbinder et al. | 128/772 |
| 4,867,174 | 9/1989 | Skribiski | 128/772 |
| 4,884,579 | 12/1989 | Engelson | 128/772 |
| 4,895,168 | 1/1990 | Machek | 128/772 |
| 4,917,102 | 4/1990 | Miller et al. | 128/772 |
| 5,095,915 | 3/1992 | Engelson | 128/772 |
| 5,111,829 | 5/1992 | Toledo | 128/772 |
| 5,129,890 | 7/1992 | Bates et al. | 128/772 |

FOREIGN PATENT DOCUMENTS

| | | |
|---|---|---|
| 0141006A1 | 5/1985 | European Pat. Off. . |
| 0347035A2 | 12/1989 | European Pat. Off. . |
| 2401668 | 8/1977 | France . |
| 1435797 | 5/1976 | United Kingdom . |

OTHER PUBLICATIONS

Train et al., "Plastic-Coated Guidewire Endourology," Journal of Endourology, vol. 2, No 4, 1988, pp. 407–409.

Takayasu et al., "Plastic Coated Guidewire for Hepatic Arteriography," Radiology, vol. 166, No. 2, 1988, pp. 545–550.

Primary Examiner—Max Hindenburg
Attorney, Agent, or Firm—Wolf, Greenfield & Sacks

[57] ABSTRACT

A guidewire having a metal wire core and a high performance plastic sleeve extruded thereover. A tapering distal portion of the metal wire core extends beyond the high performance plastic sleeve. A coil formed of radiopaque material is mounted about the distal portion. A compliant jacket covers the high performance plastic sleeve and the radiopaque coil. The compliant jacket includes a lubricious coating.

31 Claims, 1 Drawing Sheet

HIGH PERFORMANCE PLASTIC COATED MEDICAL GUIDEWIRE

CROSS-REFERENCE TO RELATED APPLICATION

This application is a continuation of copending application Ser. No. 784,921, filed on Oct. 30. 1991, which is now abandoned.

FIELD OF THE INVENTION

The invention relates to guidewires for medical applications.

BACKGROUND OF THE INVENTION

Guidewires are well known for placing and guiding catheters and other devices in lumens of the human body, such as in the vascular network. In a common type of procedure, a guidewire is inserted percutaneously into an easily accessed blood vessel. The guidewire then is manipulated to steer the guidewire through the vascular network until the distal end (the end inside the patient) reaches a desired location. The catheter may be inserted preassembled with the guidewire or the catheter may be inserted and advanced over a previously placed guidewire.

The performance of a guidewire is influenced by certain characteristics such as steerability, kink-resistance, flexibility and stiffness. The steerability of the guidewire is important especially when a tortuous path must be navigated to reach the target site as is commonly encountered when placing a catheter, such as an angioplasty catheter, in the coronary arteries. Steering is executed from the proximal end of the guidewire (outside of the patient) by rotating, pushing and pulling on the guidewire to cause corresponding movement at the distal tip of the wire. The distal tip typically is slightly bent so that when rotated the tip can be directed toward a selected one of several vascular branches. The distal tip of the guidewire commonly is radiopaque so that its movement can be observed under x-ray fluoroscopy.

Kinking is the result of a plastic deformation of the guidewire and usually is characterized by a sharp deformation or point bend of the distal section of the wire. Such a deformation may result from attempting to pass a guidewire through a relatively hard, calcified lesion, a mostly occluded vessel section or a very tortuous vascular section. The distal end of the wire may kink or bend back upon itself in a condition referred to as prolapse. Thereafter, the wire may return to its original shape, or it may remain permanently deformed if, during the bending, the wire material is stressed beyond its elastic limit.

Once kinked, the guidewire loses its controllability and usually must be discarded because the physician cannot adequately straighten the wire to remove the kink. Consequently, the procedure may have to be aborted and a new guidewire selected, reinserted, and again manipulated and advanced to the target site. Reinsertion of another guidewire increases the risk of trauma to the blood vessels and adds to the time necessary to complete the procedure. Additionally, because placement of the guidewire typically is done under X-ray fluoroscopy, the reinsertion procedure will require that the patient be exposed to additional fluoroscopic radiation.

Guidewires typically involve a balance between flexibility and stiffness characteristics. It is important that the guidewire be sufficiently flexible, particularly at its distal region, so that it does not damage the wall of the blood vessel and so that it can adapt itself to the path of the blood vessel into which it is being inserted. A stiff guidewire, however is preferred for a variety of reasons. A stiff guidewire generally provides better response of the distal end to torsional and longitudinal manipulation from the proximal end. A stiff guidewire promotes proper alignment and integrity of the catheter in relation to the blood vessel wall. A stiff guidewire is less likely to be pulled out of position in the blood vessels when the catheter is advanced over the guidewire, a characteristic referred to as "trackability".

Attempts have been made to improve the steerability, kink-resistance, flexibility and/or stiffness of medical guidewires. Often, the material or structural modifications that have enhanced a particular guidewire characteristic have adversely affected one or more of the other guidewire properties. Consequently, guidewire construction typically has involved trade-offs and compromises between the aforementioned characteristics. Guidewires historically have been made from fine stainless steel monofilament. Among the various guidewire constructions typical of the prior art are guidewires that include an elongate helical coil having an internal core wire attached at its ends to the ends of the helical coil. In another type of guidewire, such as a small diameter steerable guidewire of the type described in U.S. Pat. No. 4,545,390 (Leafy), the guidewire includes a proximal shaft formed from a solid wire having a distal tapered portion and a helical coil mounted about the distal tapered portion. Although a reduction in the diameter of the wire used to make the guidewire tends to increase flexibility it also tends to decrease stiffness with consequent reduction in manipulative and steering control. Although improvements in guidewire construction have been made, the ideal characteristics of a guidewire still requires a balancing of competing characteristics.

Psuedoelastic alloys such as Nitinol have also been used to form guidewires. Nitinol guidewires exhibit exceptional flexibility at the temperature encountered in the human body but are not easily steered because the distal tip of the guidewire cannot retain a shaped bend.

Guidewires also have been made out of plastic. While plastic guidewires tend to be more flexible than stainless steel, particularly at larger diameters, they are less kink resistant. Plastic guidewires, when packaged in the typical rolled-up coils, also suffer from permanent plastic deformation when stored in the coil over a period of time, a condition referred to as creep.

Guidewires also have been formed from combinations of metal and plastic. A thin layer or covering of a polymer, such as Teflon, has been applied to a stainless steel wire core to improve the lubricity of the guidewire. The Teflon surface coating has little appreciable affect on the kink-resistance, flexibility, steerability or stiffness of the metal core. An additional example of a guidewire formed from a combination of metal and plastic is that described in U.S. Pat. No. 3,789,841 Antoshkiw in which the guidewire is provided with a core wire surrounded by an outer plastic jacket.

SUMMARY OF THE INVENTION

The guidewire of the present invention displays improved steering, resistance to kinking, distal flexibility and/or proximal stiffness. The guidewire includes an elongated metal core wire and a high performance plastic layer which surrounds at least a portion of the metal core. In one important embodiment, the high performance plastic layer has a flexural modulus of at least 150,000 p.s.i. and an elongation at yield of at least 2%. A tapering distal portion of the elongated metal wire extends beyond the high performance plastic layer. A compliant jacket surrounds the high performance plastic layer and the distal portion of the metal wire. The compliant jacket contains or is covered with a lubricious material.

In another important embodiment of the invention, a helically wound metal spring containing a radiopaque material is mounted over the tapering distal portion of the elongated metal wire. A compliant jacket is shrink-wrapped over the high performance plastic core and the radiopaque spring. A hydrophilic material is coated on or contained within the compliant jacket.

It is among the general objects of the invention to provide a guidewire with improved steerability, flexibility, resistance to kinking and/or stiffness.

DESCRIPTION OF THE DRAWINGS

The foregoing and other objects and advantages of the invention will be appreciated more fully from the accompanying drawings in which.

DESCRIPTION OF THE PREFERRED EMBODIMENTS

Figure 1:
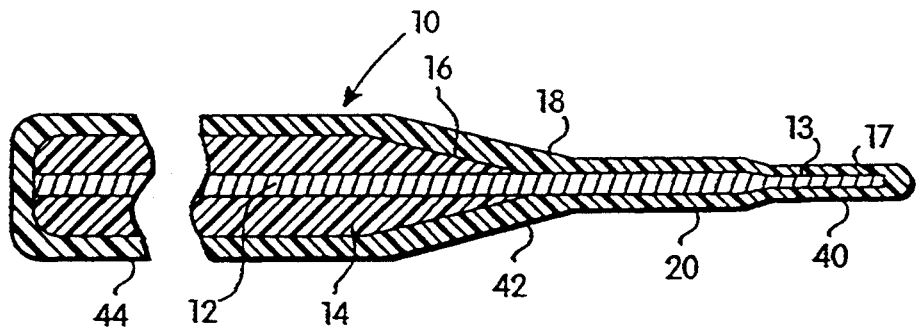
FIG. 1 is a fragmented sectional illustration of a guidewire in accordance with the invention.

The guidewire 10 shown in FIG. 1 includes an elongated metal core 12 which may be formed from type 304V stainless steel. The elongated metal core 12 also may be formed of an Inconel alloy, Monel alloy, alloy of beryllium and copper and other metals and alloys as would be apparent to those of skill in the art. The elongated metal core 12 is a fine, cold drawn wire that has been straightened and cut to the desired length. The elongated metal core 12 has a round cross-sectional shape although elliptical and rectangular cross-sectional shapes are suitable for the purposes of the invention. The distal portion 13 of the elongated metal core 12 may include a taper to improve the flexibility of the guidewire tip.

The elongated metal core 12 is covered with a sleeve 14 formed of a high performance plastic material. For the purposes of the specification and the claims, "high performance plastic" means a plastic having a flexural modulus of at least 150,000 p.s.i. and an elongation at yield of at lest 2% (elongation at yield is equal to the yield strength divided by the flexural modulus multiplied by 100). The preferred high performance plastic is a polysulfone, such as Udel P1700 distributed by Amoco Performance Products, that has a flexural modulus of approximately 360,000 p.s.i. and an elongation at yield of 2.6%. Other suitable high performance plastics include polyimide, polyetheretherketone, polyarylene ketone, polyphenylene sulfide, polyarlene sulfide, polyamideimide, polyetherimide, polyimidesulfone, polyarylsulfone, polyarylethersulfone and polyester.

The sleeve of high performance plastic 14 is bonded to the elongated metal core 12 by a thin layer of epoxy adhesive, such as TRA-BOND F113, distributed by Tra-Con, Inc. of Medford, Massachusetts, or other metal/plastic bonding material. Also suitable for joining the high performance plastic core 14 and the elongated metal core 12 is an over-extrusion process in which the high performance plastic sleeve 14 is extruded over the elongated metal core 12. Alternatively, the high performance plastic material may be applied to the elongated metal core 12 by spraying, dipping or other conventional methods for coating plastic onto metal substrates. Surface preparation of the elongated metal core 12, such as roughening or cleaning, is optional and depends upon the joining process selected and the metal core and plastic materials being utilized.

The tapering distal end 16 of the high performance plastic sleeve 14 terminates proximally to the tapering distal portion 13 of the elongated metal core 12. The tip 17 of the distal portion 13 is bendable into a configuration that facilitates steering of the guidewire. A compliant jacket 18 covers the high performance plastic sleeve 14 and the elongated metal core 12 and preferably includes a lubricious surface coating 20 or, alternatively, a lubricious material which is contained within the compliant jacket 18. The compliant jacket tends to absorb frictional forces arising during tracking of the guidewire and catheter that otherwise might lead to the abrading of the lubricant from the surface of the guidewire. The compliant jacket 18 is formed of a material that adheres to both the high performance plastic sleeve 14 and the metal core 12. Preferably, the compliant jacket material is a polyurethane such as Texin 480A distributed by Mobay Corp. of Pittsburgh, Pennsylvania. The lubricious coating 20 preferably is hydrophilic. The preferred lubricious materials include a complex of polyurethane and polyvinylpyrrolidone, a complex of polyurethane and polyethylene oxide, and mixtures thereof. Other low friction or lubricious coatings and/or materials also can be used as would be apparent to those of skill in the art.

The lubricious material selected depends upon the composition of the compliant jacket and the range of lubricity required for the particular application. The compliant jacket 18 preferably is coated with the lubricious material and then is applied to the high performance plastic sleeve 14 and the elongated metal core 12. The lubricious coating may be limited to only the distal portion 40 of the compliant jacket 18 or to only the distal portion 40 and an intermediate portion 42 of the compliant jacket 18. The proximal portion 44 of the guidewire that is manipulated by the physician does not receive a lubricious coating. The surface coating can be applied by spraying, dipping and other conventional methods.

The compliant jacket 18 is shrinkwrapped over the high performance plastic sleeve 14 and the metal core 12. In that procedure, the combination of the metal core 12 and the high performance plastic sleeve 14 is inserted into a pressurized closed ended tube of compliant material. A housing, such as a metal or plastic hypodermic tube, may be used to support the pressurized compliant jacket. The proximal end of the support tube may be fitted to a manifold through which the high performance covered metal core is advanced. The manifold may also serve to introduce the pressurized gas to the compliant tubular jacket. Alternatively, the compliant jacket 18 may be joined to the high performance plastic sleeve 14 and the metal core 12 by chemical or adhesive bonding according to recognized methods. The compliant jacket 18 includes a closed rounded end 43 that renders the distal end of the guidewire atraumatic.

Figure 2:
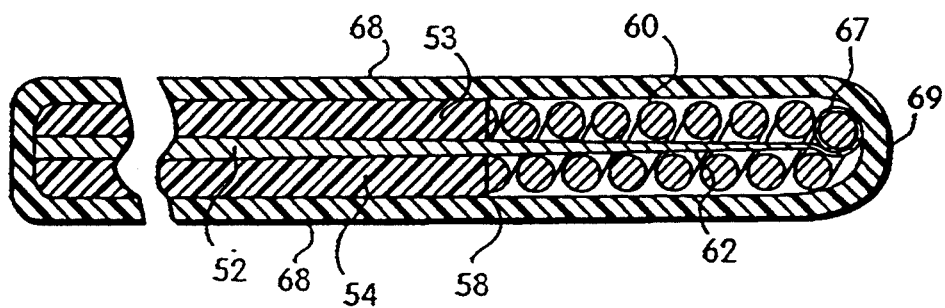
FIG. 2 is a sectional illustration of a guidewire according to another embodiment of the invention.

Another embodiment of the guidewire according to the present invention is shown in FIG. 2 and includes an elongated type 304V stainless steel metal wire 52 and a polysulfone plastic sleeve 54 extruded thereover. The distal end 53 of the high performance plastic sleeve 54 may include an epoxy resin bead 58 to ensure a secure attachment of the sleeve end 53 to the metal wire 52.

Figure 3:
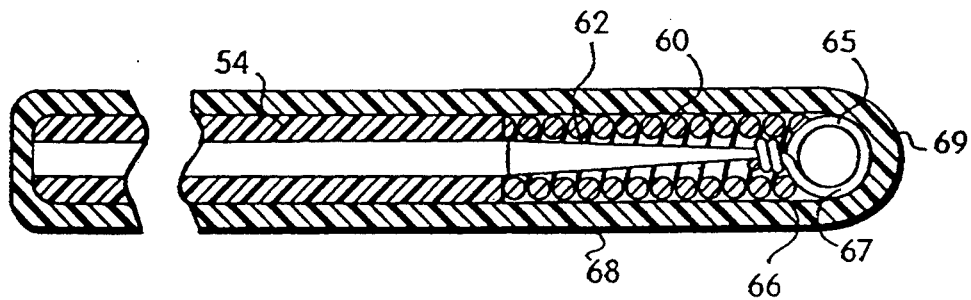
FIG. 3 is a sectional illustration of the distal tip of the guidewire shown in FIG. 2.

A radiopaque spring 60, preferably a flexible coiled wire formed of tungsten, gold, platinum or alloys thereof, is mounted about the distal portion 62 of the metal wire 52. The distal portion 62 gradually tapers commencing approximately one cm from the distal end of the high performance plastic sleeve 54. The distal portion 62 is bendable into a configuration that facilitates advancement along the vessel path. The radiopaque spring 60 may be attached to the distal portion 62 of the metal wire 52 by brazing, soldering, welding and other recognized methods. Alternatively, as illustrated in FIG. 3, the distal tip 67 of the stainless steel wire 52 may include a double loop arrangement 65 which is wider than the inner diameter of the radiopaque spring 60. The dimensions of the double loop 65 prevent axial movement of the spring 60 beyond the distal tip 67. The distal end 66 of the radiopaque spring 60 may be rounded to provide an atraumatic surface at the distal tip of the guidewire. The outer diameter of the radiopaque spring 60 approximates the outer diameter of the high performance plastic sleeve 54.

A compliant jacket 68 is shrinkwrapped over the high performance plastic sleeve 54 and the radiopaque spring 60. The compliant jacket 68 terminates in a closed rounded end 69 that extends slightly beyond the distal tip 67. The closed rounded end 69 may be filled with an epoxy resin to bond the distal wire core tip 67, the double-looped tip 65 of the radiopaque spring 60 and the compliant jacket 68. The compliant jacket 68 preferably has a uniform diameter. A lubricious coating covers the compliant jacket 68. Alternatively, a lubricious material may be contained within the compliant jacket.

Spaced indicia, corresponding to the guidewire length as measured from the distal tip to the proximal end, are marked on the polysulfone surface. The markings on the guidewire assist the physician in gauging the length of the guidewire already inserted into a patient. The location of the guidewire tip also can be determined fluoroscopically because of the radiopaque characteristic of the spring 60.

In the case of the peripheral vascular network guidewire shown in FIG. 2, the diameter of the guidewire ranges between 0.028 and 0.035 inches with the preferred diameter being approximately 0.035 inches. The elongated type 304V stainless steel wire core has a diameter between 0.010 and 0.018 inches and, preferably, has a diameter of 0.014 inches which tapers down to a distal tip diameter of 0.007 inches. The high performance plastic sleeve has an inner diameter of approximately 0.015 inches and an outer diameter of approximately 0.028 inches. The compliant jacket has an outer diameter of 0.028 to 0.035 inches. The lubricious coating with a thickness of no more than 0.0005 inches has negligible effect on the dimensions of the guidewire.

The guidewire shown in FIG. 2 is approximately sixty inches long. The proximal, non-lubricious coated section is approximately 7.875 inches long, the intermediate section is about 47.5 inches long and the tapering distal section is approximately 3.75 inches long. The radiopaque spring is slightly longer than the tapering distal section, approximately 4.15 inches.

It should be understood that the foregoing description of the present invention is intended merely to be illustrative thereof and that other equivalents, embodiments and modifications of the invention may be apparent to those skilled in the art.

What is claimed is:

1. A medical guidewire comprising:
   an elongated metal core; and
   a plastic layer surrounding said elongated metal core at least partially along its length thereof, said plastic layer having a flexural modulus which does not degrade below 150,000 p.s.i. after exposure to an aqueous environment at a temperature of approximately 37° C., such as human blood, and an elongation at yield of at least 2%.

2. The medical guidewire recited in claim 1 wherein said plastic layer and said elongated metal core are directly connected.

3. The medical guidewire recited in claim 2 wherein said plastic layer is extruded over said elongated metal core.

4. The medical guidewire recited in claim 2 wherein said plastic layer is bonded to said elongated metal core.

5. The medical guidewire recited in claim wherein a distal end of said plastic layer terminates proximal to a distal portion of said elongated metal core.

6. The medical guidewire recited in claim 5 wherein said distal end of said plastic layer tapers towards said elongated metal core.

7. The medical guidewire recited in claim 6 wherein said distal end taper is uniform.

8. The medical guidewire recited in claim 5 further including a flexible coil positioned about said distal portion of said elongate metal core.

9. The medical guidewire recited in claim 8 wherein said flexible coil contains a radiopaque material.

10. The medical guidewire recited in claim 8 wherein said flexible coil is formed from a radiopaque metal wire.

11. The medical guidewire recited in claim 8 wherein a proximal end of said flexible coil is fixed to said distal end of said plastic layer.

12. The medical guidewire recited in claim 11 wherein said proximal end of said flexible coil is fixed to said distal portion of said elongated metal core.

13. The medical guidewire recited in claim 8 wherein a distal tip of said distal portion has a perimeter wider than the inner perimeter of said flexible coil.

14. The medical guidewire recited in claim 8 wherein the outer diameter of said medical guidewire is uniform along the length thereof.

15. The medical guidewire recited in claim 8 wherein at least a portion of said distal portion of said elongated metal core is tapered towards the axis thereof, 16. The medical guidewire recited in claim 1 further comprising a compliant jacket covering said plastic layer.

17. The medical guidewire recited in claim 16 wherein said compliant jacket is shrinkwrapped to said plastic layer.

18. The medical guidewire recited in claim 16 wherein said compliant jacket is formed of a polyurethane material.

19. The medical guidewire recited in claim 16 wherein said compliant jacket supports a lubricious material.

20. The medical guidewire recited in claim 19 wherein said lubricious material includes a lubricious coating on the surface of said compliant jacket.

21. The medical guidewire recited in claim 19 wherein said lubricious material is contained within said compliant jacket.

22. The medical guidewire recited in claim 19 wherein said lubricious material is hydrophilic.

23. The medical guidewire recited in claim 19 wherein said lubricious material is selected from the group of materials consisting of a complex of polyurethane, polyvinylpyrrlidone, a complex of polyurethane and poly(ethylene oxide) and mixtures thereof 24. The medical guidewire recited in claim 16 wherein said plastic layer terminates proximally to a distal portion of said elongated metal core and said compliant jacket covers said plastic layer and a said distal portion.

25. The medical guidewire recited in claim 24 wherein said distal portion includes a gradually tapering portion and said compliant jacket covering includes a gradual taper relative thereto.

26. The medical guidewire recited in claim 24 wherein said compliant jacket includes a closed rounded end extending beyond said distal end.

27. The medical guidewire recited in claim 26 wherein said closed rounded end is filled with a resin.

28. The medical guidewire recited in claim 1 wherein said plastic layer is formed from a high performance plastic.

29. The medical guidewire recited in claim 28 wherein said high performance plastic is selected from the group of materials consisting of polysulfone, polyimide, polyester, polyetheretherketone, polyarylene ketone, polyphenylene sulfide, polyarylene sulfide, polyamideimide, polyetherimide, polyimidesulfone, polyarylsulfone, and polyarylethersulfone.

30. A medical guidewire comprising:
an elongated metal wire having a tapering distal portion;
a radiopaque coil mounted about said tapering distal portion;
a high performance plastic sleeve extruded over said elongated metal wire and terminating proximal to said tapering distal portion, said high performance plastic sleeve having a flexural modulus which does not degrade below 150,000 p.s.i. after exposure to an aqueous environment at a temperature of approximately 37° C., such as human blood, and an elongation at yield of at least 2%.
a compliant jacket shrinkwrapped over said high performance plastic sleeve and said radiopaque coil; and
a lubricious material supported by said compliant jacket.

31. A medical guidewire comprising:
an elongated core formed from a non-superelastic metal; and
a plastic layer surrounding said elongated non-superelastic metal core at least partially along its length thereof, said plastic layer having a flexural modulus which does not degrade below 150,000 p.s.i. after exposure to an aqueous environment at a temperature of approximately 37° C., such as human blood, and an elongation at yield of at least 2%.

* * * * *